United States Patent
St. Laurent et al.

(10) Patent No.: US 9,889,111 B2
(45) Date of Patent: Feb. 13, 2018

(54) PHARMACEUTICAL COMPOSITION COMPRISING OMEGA-(ARYLSULFONYL)ALKYLNITRILE

(71) Applicant: OLATEC THERAPEUTICS LLC, New York, NY (US)

(72) Inventors: Joseph St. Laurent, Lakeville, MA (US); Gerald S. Jones, Norwood, MA (US); David M. Bresse, Middleboro, MA (US)

(73) Assignee: OLATEC THERAPEUTICS LLC, New York, NY (US)

( * ) Notice: Subject to any disclaimer, the term of this patent is extended or adjusted under 35 U.S.C. 154(b) by 0 days.

(21) Appl. No.: 15/339,196

(22) Filed: Oct. 31, 2016

(65) Prior Publication Data
US 2017/0105962 A1 Apr. 20, 2017

Related U.S. Application Data

(63) Continuation of application No. 14/554,848, filed on Nov. 26, 2014, now Pat. No. 9,481,644, which is a continuation-in-part of application No. 13/909,957, filed on Jun. 4, 2013, now abandoned.

(60) Provisional application No. 61/655,916, filed on Jun. 5, 2012, provisional application No. 61/909,762, filed on Nov. 27, 2013.

(51) Int. Cl.
| | | |
|---|---|---|
| *A61K 31/277* | (2006.01) | |
| *A61K 9/14* | (2006.01) | |
| *A61K 9/06* | (2006.01) | |
| *A61K 47/10* | (2017.01) | |
| *A61K 47/34* | (2017.01) | |
| *A61K 47/32* | (2006.01) | |
| *A61K 9/00* | (2006.01) | |
| *A61K 47/14* | (2017.01) | |

(52) U.S. Cl.
CPC .......... *A61K 31/277* (2013.01); *A61K 9/0014* (2013.01); *A61K 9/0053* (2013.01); *A61K 9/06* (2013.01); *A61K 47/10* (2013.01); *A61K 47/14* (2013.01); *A61K 47/32* (2013.01); *A61K 47/34* (2013.01)

(58) Field of Classification Search
CPC ...... A61K 31/277; A61K 47/10; A61K 47/32; A61K 9/0014; A61K 9/06; A61K 9/2054; C07C 317/32
See application file for complete search history.

(56) References Cited

U.S. PATENT DOCUMENTS

| | | | |
|---|---|---|---|
| 4,424,167 A | 1/1984 | Oeckl | |
| 4,996,193 A * | 2/1991 | Hewitt | A61K 9/0014 514/20.5 |
| 5,175,192 A | 9/1992 | Ulrich et al. | |
| 5,959,019 A * | 9/1999 | Riesgraf | A61K 8/25 424/78.02 |
| 8,367,871 B2 | 2/2013 | Katsuki et al. | |
| 8,476,316 B2 | 7/2013 | St. Laurent | |
| 2009/0270470 A1 | 10/2009 | Jonasson et al. | |
| 2010/0221336 A1 | 9/2010 | Fink et al. | |
| 2010/0240756 A1 | 9/2010 | St. Laurent | |
| 2011/0251135 A1 | 10/2011 | Kuwada | |

FOREIGN PATENT DOCUMENTS

| | | |
|---|---|---|
| WO | WO 2007/103273 A2 | 9/2007 |
| WO | WO 2013/184755 A2 | 12/2013 |

OTHER PUBLICATIONS

Non-Final Office Action dated Apr. 14, 2016 in U.S. Appl. No. 13/909,957.
Hurd et al., "reactions of Mercaptans with Acrylic and Methacrylic Derivatives," J. Am. Chem. Soc., 1947, 69 (10), pp. 2328-2335.
International Search Report and Written Opinion of International Application No. PCT/US2013/044157 dated Sep. 23, 2013.
Juliana et al.; "Anti-inflammatory Compounds Parthenolide and Bay 11-7082 Are Direct Inhibitors of the Inflammasome"; The Journal of Biological Chemistry; vol. 285, No. 13, pp. 9792-9802 (Mar. 26, 2010).
Lieder, et al.; "Identification of UV-protective Activators of Nuclear Factor Erythroid-derived 2-Related Factor 2 (Nrf2) by Combining a Chemical Library Screen with Computer-based Virtual Screening"; The Journal of Biological Chemistry; vol. 287, No. 39, pp. 33001-33013 (Sep. 21, 2012).
Moskvichev, et al., "Synthesis of 2-Substituted Benzimidazoles, Benzoxazoles, and Benzothiazoles from Arylsulfonyl(thio)propionitriles,") Chemistry of Hetercoyclic Compounds, 2001; 37(9): pp. 1162-1167.
STN Registry: 100727-35-3, 14223-22-4. Published Nov. 16, 1984.

* cited by examiner

*Primary Examiner* — Sreeni Padmanabhan
*Assistant Examiner* — Jody Karol
(74) *Attorney, Agent, or Firm* — Perkins Coie LLP; Viola T. Kung

(57) ABSTRACT

The present invention is directed to a pharmaceutical composition comprising a pharmaceutically acceptable carrier and a ω-(arylsulfonyl)alkylnitrile compound, or a pharmaceutically acceptable salt thereof. The present invention is also directed to a method for treating inflammation, inflammatory-related disorders, or pain, by administering an ω-(arylsulfonyl)alkylnitrile compound or a pharmaceutically acceptable salt or solvate thereof to a subject in need thereof.

10 Claims, No Drawings

PHARMACEUTICAL COMPOSITION COMPRISING OMEGA-(ARYLSULFONYL)ALKYLNITRILE

This application is a continuation of U.S. application Ser. No. 14/554,848, filed Nov. 26, 2014; which is a continuation-in-part of U.S. application Ser. No. 13/909,957, filed Jun. 4, 2013; which claims the benefit of U.S. Provisional Application No. 61/655,916, filed Jun. 5, 2012. This application also claims the benefit of U.S. Provisional Application No. 61/909,762, filed Nov. 27, 2013. The contents of the above-identified applications are incorporated herein by reference in their entireties.

FIELD OF THE INVENTION

The present invention relates to a pharmaceutical composition comprising a pharmaceutically acceptable carrier and an ω-(arylsulfonyl)alkylnitrile compound, or its pharmaceutically acceptable salts. The present invention also relates to methods of using the compound for treating inflammation or inflammatory-related disorders and pain.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, such as mediators and antigens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Based on the physical causes, pain can be divided into three types: nociceptive, neuropathic, and mix-type.

Nociceptive pain is the term for pain that is detected by specialized sensory nerves called nociceptors. These nerves are located throughout the soft tissues, such as muscles and skin, as well as the internal organs. There are two types of nociceptive pain: somatic pain and visceral pain. Visceral pain comes from the internal organs. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Nociceptive pain is usually short in duration and end when the damage recovers. Examples of nociceptive pain include postoperative pain, sprains, bone fractures, burns, bumps, bruises, and inflammatory pain.

Neuropathic pain is pain caused by damage or disease that affects the somatosensory system. Neuropathic pain is originated from spontaneous ectopic neuron discharge in the nervous system either in central or in peripheral. Because the underlying etiologies are usually irreversible, most neuropathic pain are chronic pain. Most people describe neuropathic pain as shooting, burning, tingling, lancinating, electric shock qualities, numbness, and persistent allodynia. The nomenclature of neuropathic pain is based on the site of initiating nervous system with the etiology; for examples, central post-stroke pain, diabetes peripheral neuropathy, post-herpetic (or post-shingles) neuralgia, terminal cancer pain, phantom limb pain.

Mix-type pain is featured by the coexistence of both nociceptive and neuropathic pain. For example, muscle pain trigger central or peripheral neuron sensitization leading to chronic low back pain, migraine, and myofacial pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapy is directed to some or all of the pathogenic components of inflammation. For example, corticosteroids have a broad spectrum of activities and NSAIDS are more specifically anti-prostaglandin and analgesic. All current therapies have relatively high rates of adverse effects and adverse effects are severe and serious.

There is a need for a composition and a method for treating inflammation, inflammatory-related disorders, and pain. The composition should be economic and easy to manufacture, and the method should be effective and have no significant side effects.

SUMMARY OF THE INVENTION

The present invention is directed to a pharmaceutical composition comprising a pharmaceutically acceptable carrier and a 3-(arylsulfonyl)propanenitrile compound or a pharmaceutically acceptable salt or solvate thereof. The compound is at least 90% pure (w/w).

The present invention is also directed to a method for treating inflammation, inflammatory-related disorders, and pain. The method comprises the step of administering a 3-(arylsulfonyl)propanenitrile compound or a pharmaceutically acceptable salt thereof to a subject in need thereof. The pharmaceutical composition comprising the active compound can be applied by any accepted mode of administration including topical, oral, and parenteral (such as intravenous, intramuscular, subcutaneous or rectal). Topical administration and oral administration are preferred.

DETAILED DESCRIPTION OF THE INVENTION

Definition

"Alkyl" refers to groups of from 1 to 12 carbon atoms, either straight chained or branched, preferably from 1 to 8 carbon atoms, and more preferably 1 to 6 carbon atoms.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms in the alkyl moiety and from 6 to 10 carbon atoms in the aryl moiety. Such arylalkyl groups are exemplified by benzyl, phenethyl and the like.

"Cycloalkyl" refers to cyclic alkyl groups of from 3 to 12 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, ethanol, 1-propanol, isopropanol, 1-butanol, isobutanol, tert-butanol, acetone, methyl ethyl ketone, and diethyl ether.

ω-(Arylsulfonyl)lalkylnitriles

The inventors have discovered that ω-(arylsulfonyl)alkylnitriles (or ω-(arylsulfonyl)alkanenitriles) of Formula I, or a pharmaceutically acceptably salt or solvate thereof, are effective for treating inflammation, inflammatory-related disorders, and pain.

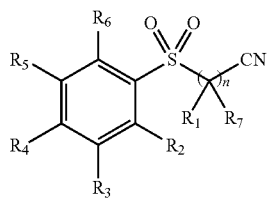

Formula I wherein n=1-6;

$R_1$ and $R_7$ are independently H, straight-chain alkyl, branched alkyl, cycloalkyl, and arylalkyl;

$R_2$-$R_6$ are independently selected from the group consisting of H, $C_{1-6}$alkyl (e.g., methyl, ethyl, n-propyl, i-propyl, n-butyl, i-butyl, sec-butyl, t-butyl), cycloalkyl (e.g., cyclopentyl, cyclohexyl), phenyl, substituted phenyl, arylalkyl (e.g. benzyl), halogen (e.g. fluoro, chloro, bromo, iodo), cyano, carboxy, carboxyamido, acetyl, hydroxyl, $C_{1-6}$alkoxyl (e.g., methoxy), trifluoromethoxy, thio, methylthio, methylsulfinyl, methylsulfonyl, nitro, amino, $C_{1-6}$alkylamino (e.g., methylamino, dimethylamino), acetamido, fluoromethyl, chloromethyl, bromomethyl, iodomethyl, trifluoromethyl, trifluoromethoxy, cyanomethyl, carboxymethyl, hydroxymethyl, methoxymethyl, thiomethyl, aminomethyl, nitromethyl, acetamido; or $R_2$ and $R_3$ are connected so as to produce a fused, bicyclic ring structure, e.g., naphthyl; or $R_3$ and $R_4$ are connected so as to produce a fused, bicyclic ring structure, e.g., naphthyl; or $R_4$ and $R_5$ are connected so as to produce a fused, bicyclic ring structure, e.g., naphthyl; or $R_2$-$R_6$ are independently a substituent that increases the electron density of the aromatic ring(s) by virtue of an electron releasing effect, either inductively or through resonance.

In one embodiment, $R_2$-$R_6$ are independently H, $C_{1-6}$alkyl, $C_{1-6}$alkoxy, amino, or halogen.

In one embodiment, $R_4$-$R_5$ and the phenyl ring form a naphthyl, optionally substituted with $C_{1-6}$ alkyl, amino, or halogen.

Preferred ω-(arylsulfonyl)alkylnitriles useful for the present invention are 3-(arylsulfonyl)propanenitrile compounds of formula II, or a pharmaceutically acceptably salt or solvate thereof:

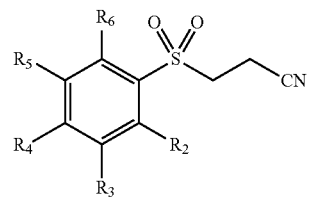

Formula II

Preferred ω-(arylsulfonyl)alkylnitriles useful for the present invention also include 3-(arylsulfonyl)propanenitrile compounds of formula III, or a pharmaceutically acceptably salt or solvate thereof,

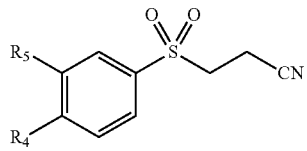

Formula III wherein $R_4$ and $R_5$ are independently H, $C_{1-6}$alkyl, $C_{1-6}$alkoxy, amino, or halogen; or $R_4$ and $R_5$ are connected so as to produce a fused, bicyclic ring structure, e.g., naphthyl.

Some of the preferred compounds include 3-(phenylsulfonyl)propionitrile (molecule weight MW=195.24, A), 3-[(4-methylphenyl)sulfonyl]propionitrile (MW=209.26, B), 3-(naphthalene-2-sulfonyl)propionitrile (MW=245.30, C), 3-[(4-chlorophenyl)sulfonyl]propionitrile (MW=229.68, D), 3-(4-methoxyphenyl)sulfonylpropionitrile (MW=225.26, E) and 3-(3,4-dichlorophenyl)sulfonylpropionitrile (MW=264.13, F) as shown below.

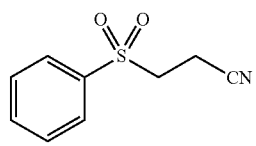

A

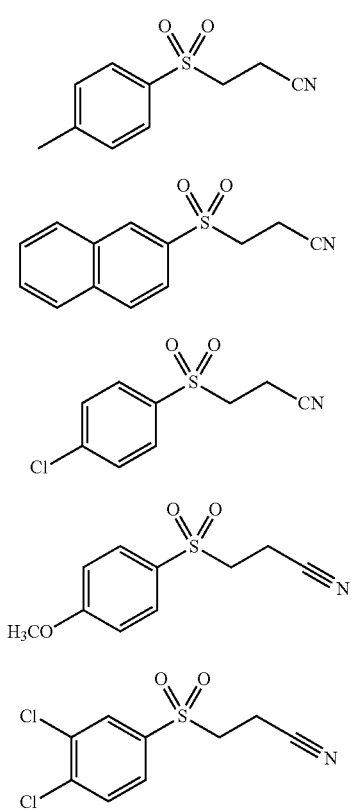

ω-(Arylsulfonyl)alkylnitriles can be prepared by alkylating the appropriate thiophenol or thiophenolate anion, or naphthalenethiol or naphthalenethiolate anion with ω-bromoalkylnitrile, followed by oxidation of the products with hydrogen peroxide or other oxidizing agents (Scientia Sinica 1974, 17, 743-751). Alternatively, ω-(arylsulfonyl)alkylnitriles can be prepared by alkylation of the requisite arylsulfinic acid sodium salts, the latter of which are commercially available or can be made by known synthetic procedures.

Pharmaceutical Compositions

The present invention provides pharmaceutical compositions comprising one or more pharmaceutically acceptable carriers and an active compound ω-(arylsulfonyl)alkylnitriles of Formula I or 3-(arylsulfonyl)propanenitrile of Formula II, or a pharmaceutically acceptable salt, or solvate thereof. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated (solubilized or suspended) into any acceptable carrier, including creams, gels, lotions, ointments or other types of vehicles that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but are not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent). Inactive ingredients that can be used with the active compounds to form a gel formulation for example include, but not limited to, diethylene glycol monoethyl ether, phenyl trimethicone, silica silylate, acrylates/$C_{10-30}$ alkyl acrylate crosspolymer, and water. Inactive ingredients that can be used with the active compounds to form a cream formulation for example include, but not limited to, mineral oil, vegetable oil, petrolatum, cetostearyl alcohol, cetearyl alcohol, sodium lauryl sulfate, sodium polyacrylate, propylene glycol, dicaprylyl carbonate, tocopherol, cetearyl isononanoate, ceteareth-20, glyceryl monostearate, glycerin, POE cetyl/stearyl ether, cetyl palmitate, $C_{12-15}$ alkyl benzoate, phenyl trimethicone, octisalate, tocopheryl acetate, panthenol, cyclopentasiloxane and dimethiconol, and water.

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve ≥90%, preferably ≥95% purity; the high purity mitigates the presence of hydrolytic and oxidative agents. In addition, DMSO at 0.1-20%, or 0.5-10% (w/w) in the formulation provides suitable solubility of the active compound.

In another embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid resides in many cell membranes. When arachidonic acids are cleaved from the membranes, it can produce many of the known eicosanoids including prostaglandins and leukotrienes, which are known pro-inflammatory entities.

The active compounds are effective in inhibiting pro-inflammatory cytokine release (e.g., IL-1β, IL-1 receptor antagonist, IL-6, TNFα, IL-4 and IFNγ) from human peripheral blood mononuclear cells in vitro. The active compound is anti-inflammatory when applied topically in the mouse ear swelling model, in which the inflammation is induced by arachidonic acid.

The present invention is directed to a method of treating inflammation and/or pain. The active compound can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation.

In one embodiment, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. "The active compound," as used herein, is intended to include the compound and its pharmaceutically acceptable salts or solvate thereof. The skeletal or muscular diseases or conditions include musculoskeletal sprains, musculoskeletal strains, tendonopathy, peripheral radiculopathy, arthritis, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

In one embodiment, the present invention is directed to a method of treating inflammation and/or pain associated gout. Gout is a chronic inflammatory disease that is characterized by recurrent, sudden, and severe attacks of acute inflammation (redness and tenderness) and pain at the joints, often at the base of the big toe. Gout is caused by elevated levels of uric acid in the blood. Gout is a type of arthritis. Some people may develop chronic gout, which is also called gouty arthritis.

The present invention provides a method for treating inflammation and/or pain associated with inflammatory skin diseases such as dermatitis, psoriasis, and acne. The method comprises the steps of identifying a subject in need thereof, and administering to the subject the active compound, in an amount effective to treat inflammation and/or pain.

The present invention further provides a method for treating inflammatory skin diseases such as dermatitis, psoriasis, and acne (Acne vulgaris). The method comprises the steps of identifying a subject in need thereof, and administering to the subject the active compound, in an amount effective to reduce or eliminate the symptoms of the disease.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

Dermatitis (also called eczema) is generic inflammation of the skin. Specific types of dermatitis include atopic, contact, nummular, and photo-induced.

Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Atopic dermatitis is a genetically determined disease that is part of the broader disease complex of atopy that includes asthma, hay fever, and atopic dermatitis. Many individuals with atopic dermatitis have various mutations of the filaggrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate an acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematosus, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by *Propionibacterium acnes* bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. Thus initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

ω-(Arylsulfonyl)alkylnitriles, which are effective in inhibiting arachidonic acid induced inflammation and in inhibiting the release of pro-inflammatory cytokine, are effective to treat inflammation and/or pain associated with psoriasis, acne, rosacea, and dermatitis, such as contact dermatitis, and atopic dermatitis.

ω-(Arylsulfonyl)alkylnitriles, which are effective in inhibiting arachidonic acid induced inflammation and in inhibiting the release of pro-inflammatory cytokine, are effective to treat inflammatory skin diseases such as dermatitis (atopic dermatitis), psoriasis, acne, and rosacea.

ω-(Arylsulfonyl)alkylnitriles are effective in treating atopic dermatitis and alleviating one or more symptoms selected from the group consisting of erythema, induration, lichenification, scaling, and oozing and crusting. ω-(Arylsulfonyl)alkylnitriles are effective in treating psoriasis and alleviating erythema, scaling, and/or thickness of the psoriasis lesions. ω-(Arylsulfonyl)alkylnitriles are effective in treating acne and alleviating acne lesions selected from the groups consisting of closed comedones, papules, pustules, nodules, and cysts. ω-(Arylsulfonyl)alkylnitriles are effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of active compounds delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 0.5-100, or 1-50, and preferably 1-10, 1-5, or 5-50 mg/kg/day, depending on the patient's condition. For example, the active compound can be applied orally to an adult human at 20-1000 mg/dosage, 20-500 mg/dosage, 100-800 mg/dosage, or 200-600 mg/dosage, 1-4 times a day, depends on the patient's condition.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1. Preparation of 3-(4-methoxyphenyl)sulfonylpropionitrile 3-(4-Methoxyphenyl)sulfonylpropionitrile can be synthesized by alkylation of 4-methoxythiophenol with 3-bromopropionitrile under basic conditions, followed by peroxide oxidation of the intermediate sulfide.

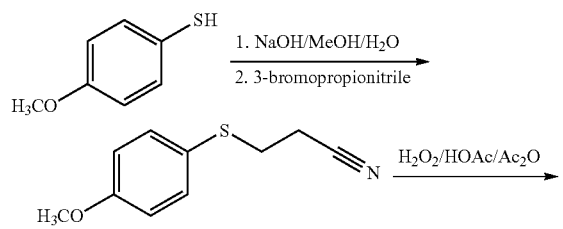

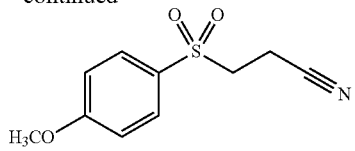

(A) 3-Bromopropionitrile (6.3 mmol) was slowly added to a mixture of 4-methoxythiophenol (7.3 mmol) and sodium hydroxide (8.3 mmol) in aqueous methanol (2:1). After stirring overnight, the upper layer of the reaction mixture, which contained predominately 3-(4-methoxyphenyl)thiopropionitrile, was isolated.

(B) Without further work-up, the product from part (A) was diluted with acetic acid (1.5 mL) and acetic anhydride (4.1 mL) and slowly treated with 30% hydrogen peroxide (~2.2 equivalents). After stirring for 3 hours, the reaction mixture was concentrated under reduced pressure to give a white solid, which was crystallized from hot ethanol (0.84 g, 59% based on 3-bromopropionitrile). FTIR-ATR: 2246.69 cm-1 (CN); 1263.48 cm-1 (SO2); 1135.88 cm-1 (SO2); HPLC-MS (API-ES positive mode): 99.0%; GC-FID: 99.3%; MS m/z 226 (M+1).

Example 2. Preparation of 3-(3,4-dichlorophenyl)sulfonylpropionitrile 3-(3,4-Dichlorophenyl)sulfonylpropionitrile can be synthesized by the alkylation of sodium (3,4-dichlorophenyl)sulfinate with 3-bromopropionitrile or by the alkylation of 3,4-dichlorothiophenol with 3-bromopropionitrile under phase transfer conditions, followed by peroxide oxidation of the intermediate sulfide.

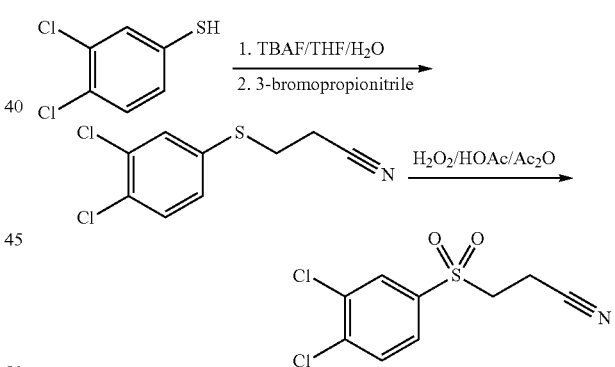

(A) 3-Bromopropionitrile (3.1 mmol) was added in portions to a mixture of 3,4-dichlorothiophenol (3 mmol) and tetrabutylammonium fluoride (3 mmol) in tetrahydrofuran containing ~5% water, such that the temperature of the reaction mixture remained below 40° C. After ~15 min, the reaction mixture was poured into ice-water, transferred to a separatory funnel, and extracted with ether. The ether extract was dried with anhydrous sodium sulfate, and concentrated under reduced pressure to a yellow oil (0.570 g).

(B) The product from part (A) was diluted with acetic acid (1 mL) and acetic anhydride (1 mL) and treated with 30% hydrogen peroxide (~3 equivalents), which was added in portions such that the temperature of the reaction mixture remained below 40° C. After stirring overnight, the reaction mixture was diluted with water and vacuum filtered to isolate a white solid that was washed with water and air-dried. The crude product was crystallized form boiling ethanol (0.394 g; 50% based on 3,4-dichlothiophenol). mp 137.7-140.2° C.; FTIR-ATR: 2256.25 cm$^{-1}$ (CN); 1299.76 cm$^{-1}$ (SO$_2$); 1130.20 cm$^{-1}$ (SO$_2$); $^1$H NMR (400 MHz; DMSO-d$_6$): δ 2.91 (t, 2H), 3.86 (t, 2H), 798-7.92 (dd, 1H], 7.96-8.02 (d, 1H), 8.16-8.20 (d, 1H); $^{13}$C NMR (100 MHz; DMSO-d$_6$): δ 11.34, 49.35, 117.57, 128.14, 130.04, 131.84, 132.53, 137.63, 138.15; MS m/z 264 (M+1; 100), 266 (M+3; 66); Anal. Calcd for C$_9$H$_7$Cl$_2$NO$_2$S (264.13): C, 40.93; H, 2.67; N, 5.30. Found: C, 40.94; H, 2.66; N, 5.32.

Example 3. Gel Formulations

Tables 1 and 2 exemplify two clear, homogeneous gel formulations containing an active compound. Active compounds include 3-(arylsulfonyl)propanenitriles, such as 3-(phenylsulfonyl)propionitrile, 3-[(4-methylphenyl)sulfonyl]propionitrile, 3-(naphthalene-2-sulfonyl)-propionitrile, 3-[(4-chlorophenyl)sulfonyl]propionitrile, which are purchased from Aldrich Rare Chemical Collection. Active compounds also include 3-(4-methoxyphenyl)sulfonylpropionitrile (Example 1) and 3-(3,4-dichlorophenyl)sulfonylpropionitrile (Example 2).

TABLE 1

|  | Gel |
| --- | --- |
| Active compound | 5.26% |
| TRANSCUTOL P ® (diethylene glycol monoethyl ether) | 68.48% |
| Dow CORNING ® 556 COSMETIC GRADE FLUID (Silsesquioxanes, phenyl trimethylsilyloxy-terminated) | 20.93% |
| Dow Corning VM-2270 aerogel (Trimethylated silica gel) | 5.33% |
| Total | 100.0% |

TABLE 2

|  | Gel |
| --- | --- |
| Active compound | 4.9% |
| TRANSCUTOL P ® (diethylene glycol monoethyl ether) | 73.6% |
| CARBOPOL ® Ultrez 20 polymer (Acrylates/C10-30 alkyl acrylate crosspolymer) | 1.5% |
| Water | 20% |
| Total | 100.0% |

Example 4. Cream Formulations

Tables 3-5 exemplify three cream formulations containing an active compound. Active compounds include 3-(arylsulfonyl)propanenitriles, such as 3-(phenylsulfonyl)propionitrile, 3-[(4-methylphenyl)sulfonyl]propionitrile, 3-(naphthalene-2-sulfonyl)-propionitrile, 3-[(4-chlorophenyl)sulfonyl] propionitrile, which are purchased from Aldrich Rare Chemical Collection. Active compounds also include 3-(4-methoxyphenyl)sulfonylpropionitrile (Example 1) and 3-(3,4-dichlorophenyl)sulfonylpropionitrile (Example 2).

TABLE 3

|  | Cream |
| --- | --- |
| Active compound | 1-5% |
| Mineral Oil | 10-15% |
| Petrolatum | 10-15% |
| Cetostearyl alcohol | 5-10% |
| Sodium lauryl sulfate | 1-2% |
| Isopropyl palmitate | 1-5% |
| Propylene glycol | 1-5% |
| Purified water | 50-60% |
| Total | 100.0% |

TABLE 4

|  | Cream |
| --- | --- |
| Active compound | 1-5% |
| Emulgade ® CM (cetearyl isononanoate, ceteareth-20, cetearyl alcohol, glyceryl monostearate, glycerin, polyoxyethylene cetyl/stearyl ether, cetyl palmitate) | 15-25% |
| Dicaprylyl carbonate | 3-5% |
| Vegetable oil | 1-3% |
| Sodium polyacrylate | 1-2% |
| Tocopherol | 1% |
| Purified water | 55-65% |
| Total | 100.0% |

TABLE 5

|  | Cream |
| --- | --- |
| Active compound | 1-5% |
| cetearyl alcohol, ceteareth-20 | 3-5% |
| Cetyl-stearyl alcohol | 5-7% |
| Vegetable oil | 2-5% |
| C$_{12-15}$ alkyl benzoate | 2-5% |
| Phenyl trimethicone | 1-2% |
| Octisalate | 2-5% |
| Tocopheryl acetate | 1-2% |
| Panthenol | 1-2% |
| Cyclopentasiloxane and dimethiconol | 5-10% |
| Water | 60-65% |
| Total | 100.0% |

Example 5. Anti-inflammatory Activity by Topical Application of Active Compounds in Mice 3-(Phenylsulfonyl)propionitrile, 3-[(4-methylphenyl)sulfonyl]propionitrile, 3-(naphthalene-2-sulfonyl)propionitrile, and 3-[(4-chlorophenyl)sulfonyl]propionitrile were purchased from Aldrich Rare Chemical Collection and used in this experiment.

The test compounds, indomethacin (positive control), and vehicle were evaluated for anti-inflammatory activity in a topical arachidonic acid-induced ear swelling model in mice.

Male ICR mice weighing 22±2 g were used and randomly divided. Arachidonic Acid (0.5 mg in 20 μl of acetone:ethanol/1:1) was applied topically to the anterior and posterior surfaces of the right ear of each mice. Test compounds and vehicle, as listed in Table 1 were similarly applied 30 minutes before and 15 minutes after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. ANOVA and Dunnett's test were employed to ascertain significant difference between vehicle control and treated groups. Significance is set at P<0.05 level. The results measured at 90 minutes after arachidonic acid application are summarized in Table 6.

TABLE 6

| Test Substance | Conc mM (% w/v) | Dosage Mg/20 µL | n | % Inhibition | P Value |
|---|---|---|---|---|---|
| Vehicle - acetone:ethanol (1:1) | NA | NA | 10 | NA | |
| Indomethacin (Positive control) | 14 (0.5) | 0.1 | 10 | 57 | <0.001 |
| 3-(phenylsulfonyl) propionitrile | 375 | 1.46 | 10 | 36 | <0.001 |
| 3-[(4-methylphenyl)sulfonyl] propionitrile | 375 | 1.57 | 5 | 44 | <0.001 |
| 3-(naphthalene-2-sulfonyl)propionitrile | 375 | 1.84 | 5 | 25 | 0.022 |
| 3-[(4-chlorophenyl)sulfonyl] propionitrile | 375 | 1.73 | 4 | 20 | 0.045 |

The tested compounds all resulted in a significant inhibition (20-44%) in the ear swelling induced by arachidonic acid, relative to that in the vehicle-treated group. The differences between treated mice and vehicle-treated mice were determined to be statistically significant (p-value by t-test was <0.05).

Example 6. Anti-Inflammatory Activity of Active Compound by Topical Application in Mice 3-(4-methoxyphenyl)sulfonylpropionitrile and 3-(3,4-dichlorophenyl)sulfonylpropionitrile, prepared from Examples 1 and 2, were test compounds in this experiment.

The test compounds, indomethacin (positive control), and vehicle were evaluated for anti-inflammatory activity in a topical arachidonic acid-induced ear swelling model in mice.

Male ICR mice weighing 22±2 g were used and randomly divided; the test compound and vehicle control had 10 mice, and indomethacin had 5 mice. Arachidonic Acid (0.5 mg in 20 µl of acetone:ethanol/1:1) was applied topically to the anterior and posterior surfaces of the right ear of each mouse. Test substances and vehicle, as listed in Table 4 were similarly applied 30 min before and 15 min after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. ANOVA and Dunnett's test were employed to ascertain significant difference between vehicle control and treated groups. Significance is set at P<0.05 level. The results measured at 90 minutes after arachidonic acid application are summarized in Table 7.

TABLE 7

| Test Substance | Conc mM | Dosage mg/20 µL | n | % Inhibition | P Value |
|---|---|---|---|---|---|
| Vehicle - acetone:ethanol (1:1) | NA | NA | 10 | NA | |
| Indomethacin (Positive control) | 14 | 0.1 | 5 | 58 | <0.001 |
| 3-(4-methoxyphenyl)sulfonyl-propionitrile | 375 | 1.7 | 10 | 23 | 0.014 |
| 3-(3,4-dichlorophenyl)sulfonyl-propionitrile | 375 | 2.0 | 10 | 28 | 0.001 |

3-(4-Methoxyphenyl)sulfonylpropionitrile and 3-(3,4-dichlorophenyl)sulfonylpropionitrile resulted in 23% and 28% inhibition respectively in the ear swelling induced by arachidonic acid, relative to that in the vehicle-treated group. The differences between treated mice and vehicle-treated mice were determined to be statistically significant (p-values by t-test were 0.014 and 0.001, respectively).

Example 7. Anti-Inflammatory Activity of Oral Administration of Active Compound in Mice 3-[(4-Methylphenyl)sulfonyl]propionitrile was suspended in vehicle (1% Tween 80 in water) to 3 mg/mL. The test compound, dexamethasone (positive control in vehicle), and vehicle were orally administered to mice and evaluated for anti-inflammatory activity in the topical arachidonic acid induced ear swelling model in mice.

Male ICR derived mice weighing 22±2 g were used in this experiment. 10 mice were used for each group (active compound, positive control, and vehicle). All animals were maintained in a controlled temperature (22-24° C.) and humidity (60%-70%) environment with 12-hour light/dark cycles for at least one week prior to use.

Arachidonic acid (0.5 mg in 20 µL acetone) was applied topically onto the anterior and posterior surfaces of the right ear of test animals to induce inflammation. Active compound in vehicle (10 mL/kg) and vehicle (10 mL/kg, 30 mg/kg) was orally administered by gavage 1 hour before arachidonic acid, whereas dexamethasone was orally administered by gavage 3 hour before arachidonic acid challenge. At 60 minutes and 90 minutes after arachidonic acid induction of ear edema, the thickness of the right ear and the left ear was measured and the difference calculated as an indication of the inflammation in the right ear. Significant activity was defined as a statistically significant inhibition (p-value determined by t-test was <0.05) in arachidonic acid induced ear swelling relative to the vehicle-treated group. The results at 90 minutes are shown in Table 8. Oral administration of 3-[(4-methylphenyl)sulfonyl]propionitrile caused significant inhibition in arachidonic acid induced ear swelling at 90 minutes.

TABLE 8

| Test Substance | Dosage mg/kg | n | % Inhibition | P Value |
|---|---|---|---|---|
| Vehicle (1% Tween 80 in water) | NA | 10 | NA | |
| Dexamethasone (Positive control) | 0.3 | 10 | 36 | <0.0001 |

TABLE 8-continued

| Test Substance | Dosage mg/kg | n | % Inhibition | P Value |
|---|---|---|---|---|
| 3-[(4-methylphenyl)sulfonyl]propionitrile | 30 | 10 | 16 | 0.0333 |

Other 3-(arylsulfonyl)propanenitriles can be tested by the same protocol as described in this example.

Example 8. Inhibition of Cytokine Activities (Prophetic Example)

The active compounds (3-(arylsulfonyl)propanenitriles) are tested for their inhibitory effects on in vitro cytokine release from human peripheral blood mononuclear cells (PBMCs). Secretion of cytokines by PBMCs plays a significant role in the inflammatory response.

Each active compound is added to cultures of fresh human PBMCs at 162 µM (22 µg/mL) in duplicate. One hour later, PBMCs are stimulated to secrete cytokines using the mitogens lipopolysaccharide and concanavalin A (ConA). Lipopolysaccharide at 50 pg/mL is used to stimulate the release of interleukin IL-1β, IL-6 and tumor necrosis factor TNFα. ConA at 20 µg/mL is used to stimulate the release of IL-4 and ConA at 5 µg/mL is used to stimulate interferon IFNγ. The corticosteroid dexamethasone (100 nM) is used as a positive control. After 24 hours of incubation, the supernatants are assayed for the cytokines using the Luminex Bead kit. The percent inhibition of IL-1β, IL-6, TNFα, IL-4 and IFNγ by the active compounds and the positive compound are calculated. The results demonstrate that the active compound has an inhibitory effect on cytokines involved in the inflammatory process.

Example 9. Anti-Inflammatory and Analgesic Activity of Active Compounds in a Carrageenan Model (Prophetic Example)

3-(Arylsulfonyl)propanenitriles are prepared as a gel formulation according to Example 3 or as a cream formulation according to Example 4. Test materials, 3-(arylsulfonyl)propanenitriles in gel formulation (1-5%), indomethacin (positive control), and vehicle (gel formulation without active compound) are evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. Test material (1-5%) or vehicle gel is applied to the paw topically at volumes of 0.05, 0.1 0.15 or 2.0 mL, after 1.5, 2.5, and 3.5 hours following the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments Inflammation and analgesia are measured 4 hours after carrageenan administration. Test materials are expected to have anti-inflammatory and/or analgesic properties as measured by a significant decrease in paw volume and/or a significant increase in mechanical pressure needed to elicit paw withdrawal, respectively, as compared to the vehicle control.

Example 10. Analgesic Activity of Active Compounds in a Hot Plate Model (Prophetic Example)

3-(Arylsulfonyl)propanenitriles are prepared as a gel formulation according to Example 3 or as a cream formulation according to Example 4. Active compounds in a gel or cream formulation (1-5%), morphine (positive control), and vehicle (gel formulation without active compound), are evaluated for analgesic activity in the rat hot plate model.

Rats are used in the experiment. Test material (1-5%) or vehicle gel is applied to the paw topically at volumes of 0.05, 0.1 0.15 or 2.0 mL. One hour later the rat is placed on a 55° C. hot plate, and the time to lick the paw is measured. The positive control, morphine, is given orally at 30 mg/kg, 1 hour prior to hot plate testing. Test materials are expected to have analgesic properties as measured by a significant increase in time to licking as compared to the vehicle control (t-test, p<0.05).

Example 11. Analgesic Activity of Active Compounds in CFA-Induced Thermal Hyperalgesia (Prophetic Example)

CFA (Complete Freund's Adjuvant) is known to induce inflammatory pain (Walker, et al. JPET. 304: 56-62, 2003).

Male Sprague-Dawley rats weighing 180±20 g are used. The animals, divided into groups of 8-10 each, receive a subplantar injection (0.1 ml) of CFA (0.1% solution) to the tested hindpaw at 24 hours prior to experimentation. Thermal hyperalgesia is tested by using the IITC Model-336G (IITC INC. USA) apparatus with a thermally regulated glass floors set at 30° C. Each rat is placed within a plastic box atop a glass floor. A light beam under the floor is aimed at the plantar surface of the right hind paw. The time is measured automatically when the paw is withdrawn away from the thermal stimulus. The intensity of the light is adjusted with average group baseline latency from 12 to 14 sec (pre-CFA) and a cut-off latency of 20 sec imposed. The latency to withdrawal is obtained for each rat and defined as the heat pain threshold. Twenty four hours after CFA injection, rats are pre-selected (with clear presence of thermal hyperalgesia) for experimentation only if the latency to withdrawal is less than 75% of baseline.

3-(Arylsulfonyl)propanenitriles are prepared as a gel formulation according to Example 3 or as a cream formulation according to Example 4. Active compounds in a gel or cream formulation (1-5%), active compounds in DMSO, morphine (positive control, p.o., 20 mg/kg), topical vehicle (gel formulation without an active compound), and oral vehicle (DMSO) are evaluated for analgesic activity in the formalin model.

Test substance or vehicle is either administered orally (50, 100, or 500 mg/kg in DMSO), or topically (1-5% gel formulation) to the plantar surface of the hind paw, at 60 minutes before the level of thermal hyperalgesia is again measured (post-treatment). Mean±SEM of thermal paw withdrawal time is calculated. Unpaired Student's t test is applied for comparison the values of post-treatment between test substance treated group and vehicle control group. Positive activity is considered at P<0.05.

Example 12. Analgesic Activity of Active Compounds in a Formalin Test (Prophetic Example)

Formalin test is a model of continuous pain resulting from formalin-induced tissue injury. Nociceptive and inflammatory pain is induced by injection of a dilute formalin solution into the paw, resulting in nocifensive behavior including paw flinching. The formalin model encompasses inflammatory, neurogenic, and central mechanism of pain. The early phase of pain (from 0 to about 10 minutes) is due to nociceptive mechanism and the late phase of pain (from 10-40 minutes) is due to a combination of inflammatory pain and nociceptive mechanism. Pain behavior is assessed using manual paw licking measurements. The endpoints of the study are the number of paw licking events. (Hunskaar et al., Pain, 30:103-114, 1987; Li et al., Molecular Pain, 6:11, 2010)

10 Mice per group are used in the study. Immediately prior to testing (at time 0), mice are restrained in a cloth and injected with 20 μL of a 5% formalin solution, subcutaneously into the dorsal surface of the left hind paw. Vehicle control (DMSO) and test compounds 3-(arylsulfonyl)propanenitriles (in DMSO) are administered by oral gavage to mice. The amounts of test compounds are 50, 200, or 500 mg/kg per dose.

Positive control morphine in saline is administered by subcutaneous injection at 8 mg/kg to mice, immediately before formalin injection and testing at time zero.

Following formalin injection, animals are placed in individual cages, and manually observed for 60 minutes. The licking events are recorded in five minute intervals continuously for a total of 60 minutes.

The number of licking events at different time points post formalin injection of vehicle control, morphine-treated, and test compound-treated mice are plotted in 5 minute intervals.

The numbers of licking events per minute are calculated between 0-10 minutes and 10-40 minutes for vehicle, positive control, and test compound. A statistically significant reduction of licking event per minute is an indication that the test compound is effective in treating acute nociceptive pain (early phase) or inflammatory nociceptive pain (late phase).

Example 13. Analgesic Activity of Active Compounds in Chronic Constriction Injury Model (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats weighing 180±20 g are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. J. Neuroscience Methods, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

3-(Arylsulfonyl)propanenitriles are prepared as a gel formulation according to Example 3 or as a cream formulation according to Example 4. 3-(Arylsulfonyl)propanenitriles are also prepared in DMSO (50, 200, or 500 mg/kg) for oral administration.

Test compounds in a gel or cream formulation (1-5%), test compounds in oral formulation (DMSO), morphine (positive control, p.o., 20 mg/kg), topical vehicle (gel formulation without an active compound), and oral vehicle (DMSO) are evaluated.

Test compound or vehicle is either administered orally (50, 200, or 500 mg/kg) or topically (1-5% gel formulation) to the plantar surface of the left hind paw. The mechanical allodynia test is performed 30 min before (pre-treatment) and 1 and 3 hours after a single dose of test compound or vehicle (post treatment). Paw withdraw thresholds of control and tested compounds are measured.

Example 14. Treatment of Arthritis (Prophetic Example)

Zymosan injected directly into the knee joint of mice elicits an inflammatory response and is used as a model of arthritis (Verschure et al, Ann. Rheum Dis. 53:455-460, 1994). Endpoints measured in this model include knee joint swelling score, cytokine levels in the synovial tissue and microscopic pathology of the knee.

Active compounds 3-(phenylsulfonyl)propionitrile, 3-[(4-methylphenyl)sulfonyl]propionitrile, 3-(naphthalene-2-sulfonyl)-propionitrile, 3-[(4-chlorophenyl)sulfonyl]propionitrile, 3-(4-methoxyphenyl)sulfonylpropionitrile and 3-(3,4-dichlorophenyl)sulfonylpropionitrile are each suspended in DMSO. Vehicle control (DMSO) and each active compound are administered by oral gavage to mice with a volume of 5 mL/kg. The active compounds are each administered at a dosage of 50-500 mg/kg in dimethyl sulfoxide (DMSO).

There are 5 mice per group, with a total of 10 knees injected. On Day 1, C57BL6 mice are dosed (50, 200, or 500 mg/kg/dose) with active compounds or vehicle twice on Hours 0 and 12. On Day 2, mice are dosed with active compounds or vehicle on Hour 24, then injected intra-articularly with 180 μg of zymosan (6 μL) into both knee joints on Hour 25, and then dosed a second time on Hour 36 with each active compound or vehicle. On Day 3, mice are again dosed with each active compound or vehicle on Hour 48. Two hour post-dosing on Hour 50, knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compounds are expected to result in decreased inflammation as measured by a decrease in joint swelling, decrease in cytokine levels and decrease influx of inflammatory cells to the site of inflammation.

Example 15. Treatment of Gout (Prophetic Example)

Monosodium urate monohydrate (MSU) crystals injected in combination with a free fatty acid (FFA) directly into the knee joint of mice elicits an inflammatory response and is used as a model of gout (Joosten et al, Arthritis & Rheumatism, 62(11):3237-3248, 2010)). Endpoints measured in this model include knee joint swelling score, cytokine levels in the synovial tissue and microscopic pathology of the knee.

Active compounds 3-(phenylsulfonyl)propionitrile, 3-[(4-methylphenyl)sulfonyl]propionitrile, 3-(naphthalene-2-sulfonyl)-propionitrile, 3-[(4-chlorophenyl)sulfonyl]propionitrile, 3-(4-methoxyphenyl)sulfonylpropionitrile and 3-(3,4-dichlorophenyl)sulfonylpropionitrile are each suspended in dimethyl sulfoxide (DMSO). Vehicle control (DMSO) and each active compound are administered by oral gavage to mice with a volume of 5 mL/kg. The active compounds are each administered at a dosage of 50-500 mg/kg in DMSO.

There are 5 mice per group, with a total of 10 knees injected. On Day 1, C57BL6 mice are dosed (50, 200, or 500 mg/kg/dose) with active compounds or vehicle twice on Hours 0 and 12. On Day 2, mice are dosed with active compounds or vehicle on Hour 24, then injected intra-articularly with MSU crystals (300 µg) and C18:0 FFA (200 µM)(10 µL) on Hour 25. Three hours later (Hour 28), knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compounds are expected to result in decreased inflammation as measured by a decrease in joint swelling, decrease in cytokine levels and decrease influx of inflammatory cells to the site of inflammation.

Example 16. Treatment of Knee Pain (Prophetic Example)

Objectives:

To investigate the efficacy of the active compound in a gel formulation or in an oral formulation in patients with mild to moderate knee pain associated with osteoarthritis following temporary cessation of standard NSAID therapy. The focus of this study is on the symptoms caused by painful arthritis. The clinical trial is utilizing osteoarthritis of the knee as a well-established paradigm for other musculoskeletal disorders.

Topical Formulation:

3-(Arylsulfonyl)propanenitriles are prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 100-600 mg of the active compound 3-(arylsulfonyl)propanenitriles are used in this example. Placebo capsules or tablets do not contain the active compound.

Methodology:

A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7-day washout period. Patients are then randomized in a 1:1:1 ratio (1% active gel, 5% active gel, placebo). A total of up to 150 patients are enrolled and treated for 14 days with follow-up at 14, 21, and 28 days.

The active gel or placebo is applied to the affected knee 3 times a day for 14 days for a total of 42 treatments given every 4-6 hours while awake.

The capsules or tablets are orally administered to patients 1-4 times a day for 14 days.

Patients are treated for 14 days and followed up for a further 14 days. NSAIDs may be restarted after the Day 14 visit.

Criteria for Evaluation:

Safety:

Adverse Events (AEs) throughout the study.

Physical examination at enrollment (−7 days, start of NSAID washout period), Baseline, Day 14 and Day 28.

Vital signs at enrollment (−7 days, start of NSAID washout period), Baseline and Days 7, 14, 21, 28.

Clinical laboratory measurements at Baseline, and Days 7, 14, 21 and 28.

Clinical Activity:

The primary clinical activity parameters are the measurement of pain at the site of application, as quantified by Pain on Movement assessment (100-mm VAS) and the Western Ontario and McMaster University (WOMAC) index (100-mm VAS or 5-point Likert scale). The effect of treatment on swelling, tenderness and inflammation of the knee is recorded, also the time to reduction or eradication of pain after treatment is recorded.

Study Endpoints:

The primary clinical activity endpoints are:

Change from Baseline to Day 14 in WOMAC functional disability index and sub-indices:

Pain (Scale 0-20).

Stiffness (Scale 0-8).

Physical function (Scale 0-68).

Change from Baseline (Day 1) to Day 14 in Pain on Movement (1-100 mm VAS).

The secondary clinical activity endpoints are:

Change in Current Knee Pain score (100 mm VAS) at Baseline from pre-dose to 1 hour post-dose Change in Current Knee Pain score (100 mm VAS) at Baseline from pre-dose to 2 hours post-dose Change in Global Rating of Disease (5-point Likert scale)

Time to reduction or eradication of pain subsequent to each application of active compound.

Use of rescue medication (APAP).

Proportion of subjects experiencing an improvement in Pain on Movement (100-mm VAS) from Baseline to Day 14, equal to or greater than the minimum clinically important improvement (MCII) threshold of 15 mm or 20%

Proportion of subjects whose Pain on Movement (100-mm VAS) at Day 14 is less than the Patient Acceptable Symptom State (PASS) threshold of 40 mm Proportion of subjects who are 'Responders' based on the OARSI Responder Index, in relation to WOMAC Index.

Example 17. Treatment of Atopic Dermatitis (Prophetic Example)

Objectives:

To investigate the efficacy of 3-(arylsulfonyl)propanenitriles gel in patients having atopic dermatitis.

Topical Formulation:

3-(Arylsulfonyl)propanenitriles are prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 100-800 mg of the active compound 3-(arylsulfonyl)propanenitriles are used in this example. Placebo capsules or tablets do not contain the active compound.

Methodology:

This is a randomized, double-blind, placebo controlled, parallel treatment clinical activity study.

Male and female patients with mild to severe atopic dermatitis are enrolled after discontinuation of all treatments for atopic dermatitis for a period of 4 weeks before study initiation. Patients are randomized in a 1:1 ratio (active gel, placebo). A total of 300 patients are enrolled and treated.

The active gel or placebo is applied twice a day to affected areas of the body for 12 weeks.

The capsules or tablets are orally administered to patients 1-4 times a day for 12 weeks.

The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target atopic dermatitis area of involvement for erythema, induration, lichenification, scaling, and oozing and crusting with each parameter rated on a 0-4 scale with 0=none or clear, 1=almost clear, 2=mild disease involvement, 3=moderate disease involvement, and 4=severe disease involvement.

Statistical analyses of each of these efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 18. Treatment of Psoriasis (Prophetic Example)

Objectives:

To investigate the efficacy of the 3-(arylsulfonyl)propanenitriles gel in patients having psoriasis vulgaris.

Topical Formulation:

3-(Arylsulfonyl)propanenitriles are prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 100-800 mg of the active compound 3-(arylsulfonyl)propanenitriles are used in this example. Placebo capsules or tablets do not contain the active compound.

Methodology:

This is a randomized, double-blind, placebo controlled, parallel treatment clinical activity study.

Male and female patients with mild to severe psoriasis vulgaris are enrolled. Patients discontinue all treatments for psoriasis for a period of 4 weeks before study initiation. Patients are randomized in a 1:1 ratio (active gel, placebo). A total of 200 patients are enrolled and treated.

The active gel or placebo is applied twice a day to affected areas of the body for 12 weeks.

The capsules or tablets are orally administered to patients 1-4 times a day for 12 weeks.

The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target psoriasis lesion for erythema, scaling, and thickness of each parameter rated on a 0-4 scale with 0=none or clear, 1=almost clear, 2=mild disease involvement, 3=moderate disease involvement, and 4=severe disease involvement.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 19. Treatment of Acne (Prophetic Example)

Objectives:

To investigate the efficacy of the 3-(arylsulfonyl)propanenitriles gel in patients having acne vulgaris.

Topical Formulation:

3-(Arylsulfonyl)propanenitriles are prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 100-800 mg of the active compound 3-(arylsulfonyl)propanenitriles are used in this example. Placebo capsules or tablets do not contain the active compound.

Methodology:

This is a randomized, double-blind, placebo controlled, parallel treatment clinical activity study.

Male and female patients with mild to severe acne vulgaris are enrolled. Patients discontinue all treatments for acne for a period of 4 weeks before initiation of the study. Patients are randomized in a 1:1 ratio (active gel, placebo). A total of 500 patients are enrolled and treated.

The active gel or placebo is applied twice a day to affected areas of the body for 12 weeks.

The capsules or tablets are orally administered to patients 1-4 times a day for 12 weeks.

The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after discontinuation of the study medication.

The investigator global assessment, IGA, is based upon a rating scale of 0 to 4 with 0=none or clear, 1=almost clear, 2=mild disease involvement, 3=moderate disease involvement, and 4=severe disease involvement, and:

2. separate counts of all types of acne lesions i.e. open and closed comedones, papules, pustules, nodules, and cysts.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A pharmaceutical composition comprising a pharmaceutically acceptable carrier and a compound of C, or a pharmaceutically acceptable salt thereof:

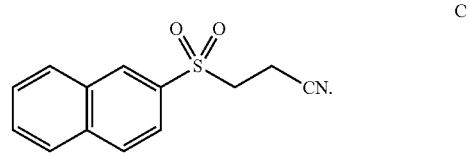 [SMILES: N#CCCS(=O)(=O)c1ccc2ccccc2c1]

C

2. The pharmaceutical composition according to claim 1, wherein the compound has at least 90% (w/w) purity, and the composition is in a topical form of gels, creams, lotions, ointments, or patches.

3. The pharmaceutical composition according to claim 2, wherein the pharmaceutically acceptable carrier is an emollient selected from the group consisting of: lauryl lactate, diethylene glycol monoethyl ether, caprylic/capric triglyceride, octisalate, silicone fluid, squalene, and sunflower oil.

4. The pharmaceutical composition according to claim 2, wherein the pharmaceutically acceptable carrier is a permeation enhancer selected from the group consisting of lactate esters and diethylene glycol monoethyl ether.

5. The pharmaceutical composition according to claim 4, further comprising acrylates/C10-30 alkyl and tris(2-hydroxyethyl)amine.

6. The pharmaceutical composition according to claim 1, wherein the compound has at least 90% (w/w) purity, and the composition is in an oral form of tablets or capsules.

7. A method of treating inflammation, comprising the steps of:
   identifying a subject suffering from inflammation, and
   administering to the subject the pharmaceutical composition of claim 1, in an amount effective to treat inflammation.

8. The method according to claim 7, wherein said method reduces or alleviates the symptoms of localized manifestations of inflammation characterized by acute or chronic swelling, pain, or redness.

9. The method according to claim 7, wherein said compound is administered by local administration or systemic administration.

10. The method according to claim 7, wherein said compound is administered by topical administration.

* * * * *